United States Patent [19]

Georgiev et al.

[11] Patent Number: 4,600,782

[45] Date of Patent: Jul. 15, 1986

[54] SUBSTITUTED SPIRO[OXAZOLIDINE-5,2′-ADAMANTANE] COMPOUNDS

[75] Inventors: Vassil S. Georgiev, Rochester; Clyde R. Kinsolving, Fairport, both of N.Y.

[73] Assignee: Pennwalt Corporation, Philadelphia, Pa.

[21] Appl. No.: 620,785

[22] Filed: Jun. 15, 1984

[51] Int. Cl.[4] .................... C07D 263/52; A61K 31/42
[52] U.S. Cl. ...................................................... 548/216
[58] Field of Search ........................................ 548/216

[56] References Cited

PUBLICATIONS

Magnus, P. et al., Synthesis, (7), pp. 575–577, (1980).
Sasaki, T. et al., Tetrahedron, 35, 1073–1078, (1979).
Narayanan, V., J. Med. Chem., 15, pp. 682–683, (6), (1972).
Lundahl, K., et al., J. Med. Chem., 15, pp. 129–132, (2), (1972).
Zinner, G., et al., Chem. Abstract, 80: 82832m.
Morat, C., et al., Tetrahedron Letters, 47, 4561–4564, (1979).

*Primary Examiner*—George F. Lesmes
*Assistant Examiner*—S. A. Gibson

[57] ABSTRACT

Substituted spiro[oxazolidine-5,2′-adamantane] compounds are described.

10 Claims, No Drawings

SUBSTITUTED SPIRO[OXAZOLIDINE-5,2'-ADAMANTANE] COMPOUNDS

BACKGROUND OF THE INVENTION

This invention relates generally to spiro[N-heterocyclic-adamantanes] and more specifically to substituted spiro[oxazolidine-5,2'-adamantane] compounds.

Of the vast amount of information on the synthesis of adamantane and its substituted analogs, only a relatively small part of it represents results dealing with the preparation of spiro[N-heterocyclic-adamantanes]. A number of spiro[pyrrolidine-3,2'-adamantane] derivatives 1 were found effective against influenza A, parainfluenza Sendai, coxsackie A21, and rhinovirus. Derivative 2 was reported active as an antimuricide agent in rats.

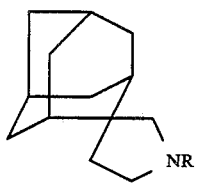

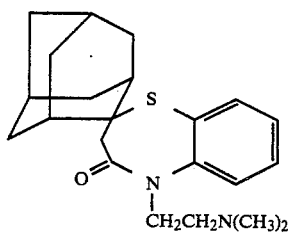

We have now prepared a new series of spiro[N-heterocyclic-adamantanes] which are substituted spiro[oxazolidine-5,2'-adamantane] derivatives.

SUMMARY OF THE INVENTION

In accordance with this invention there are provided substituted spiro[oxazolidine-5,2'-adamantane] compounds having the general formula:

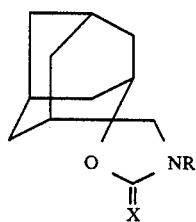

where R is selected from H, alkyl, benzoyl, and spiro[2-oxazolidinone-5,2'-adamantane]-3-thiocarbonyl; and where X is selected from oxygen and cycloalkyl in which the cycloalkyl group is attached in a spiro mode.

DETAILED DESCRIPTION

The compounds of the invention can be prepared by the reaction of 2-adamantanone (3) with sodium cyanide in methanol-concentrated sulfuric acid, followed by lithium aluminum hydride reduction of the resulting cyanohydrin derivative (4) to afford the intermediate 2-aminomethyl-2-hydroxyadamantane intermediate (5) as shown below:

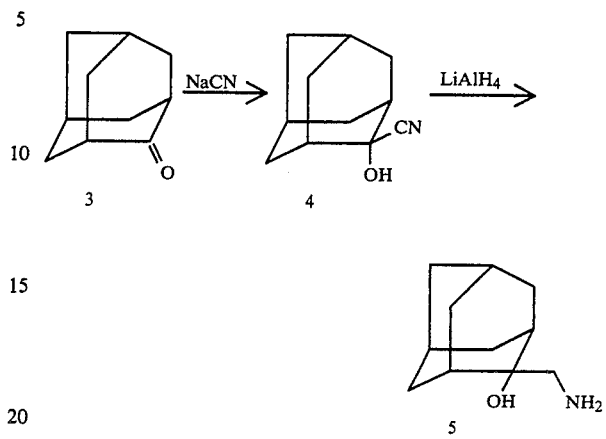

Subsequent condensation of 5 with phosgene or an appropriate alicyclic ketone provides the corresponding adamantane-spiro[oxazolidine-5,2'-adamantane] analogs I and VIII, respectively.

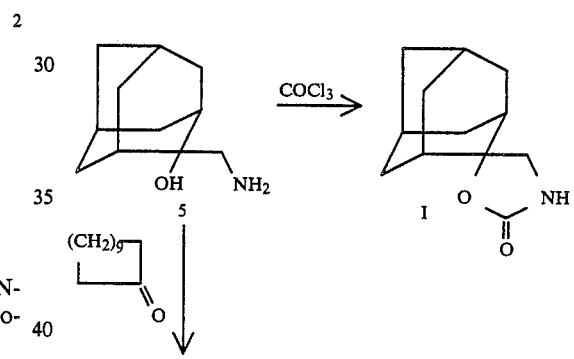

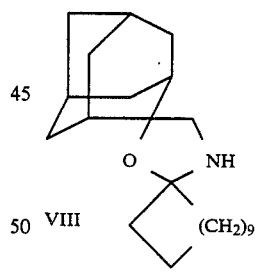

Exposure of compound I to either m-nitrobenzoyl chloride or thiophosgene provides the N-substituted analogs III and IV, respectively.

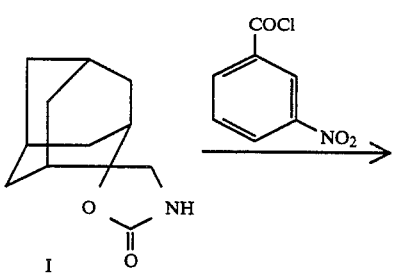

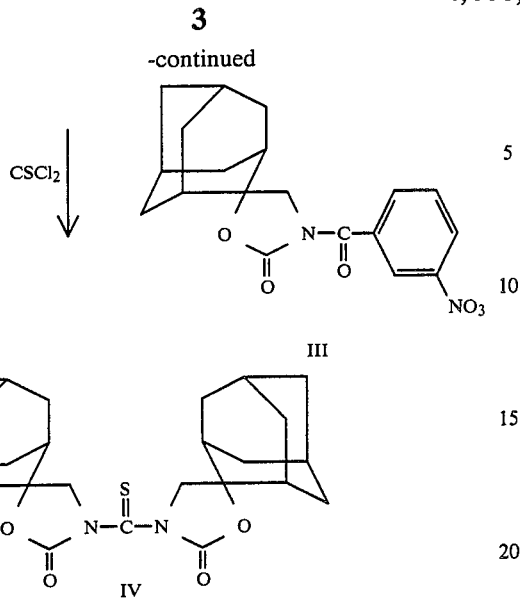

EXAMPLE 1

Preparation of Spiro[2-Oxazolidinone-5,2'-adamantane] (I)

A. Preparation of 2-Cyanoadamantan-2-ol (4)

To a well stirred solution of 2-adamantanone (45.0 grams, 0.3 mol) in 200 ml methanol were added 50 ml concentrated sulfuric acid at a rate that caused the solution to reflux. Then a saturated aqueous solution of sodium cyanide (88.2 grams, 0.6 mol) was added, and the mixture was first refluxed for 1 hour and then stirred at room temperature for 3 additional hours. Ether was added, and the organic solution was decanted from the precipitated salts. The ether solution was washed with an aqueous solution of sodium chloride and water and then dried and evaporated to leave 43.0 grams (81%) of compound 4 as a beige crystalline solid, melting point >240° C. (decomposition).

B. Preparation of 2-Aminomethyl-2-hydroxyadamantane (5)

A solution of 2-cyanoadamantan-2-ol (6.0 grams, 0.03 mol) in ether was added to a suspension of lithium aluminum hydride (3.9 grams, 0.13 mol) in ether. The reaction mixture was refluxed for 6 hours. Following workup, 4.10 grams of 2-aminomethyl-2-hydroxyadamantane were obtained as white crystals, melting point 154°–156° C. (cyclohexane).

C. Preparation of Spiro[2-Oxazolidinone-5,2'-adamantane] (I)

2-Aminomethyl-2-hydroxyadamantane (0.58 gram, 3 mmol) was refluxed for 2 hours with phosgene in toluene (25% solution, 25 ml). The solvent was evaporated leaving 0.12 gram of spiro[2-oxazolidinone-5,2'-adamantane], melting point 203°–206° C. (petr. ether).

EXAMPLE 2

Preparation of N-Methyl-spiro[2-oxazolidinone-5,2'-adamantane] (II)

Sodium methoxide (0.14 gram, 25 mmol) was added to a solution of spiro[2-oxazolidinone-5,2'-adamantane] (I) (0.41 gram, 2 mmol) in 10 ml anhydrous methanol. The mixture was stirred at room temperature for 10 minutes then the solvent was evaporated. The solid residue was dissolved in 60 ml toluene and dimethyl sulfate (0.3 ml, 3 mmol) was added. The reaction mixture was refluxed for 75 minutes. After workup, 0.69 gram of derivative II was obtained, melting point 191°–194° C. (petr. ether).

EXAMPLE 3

Preparation of N-(m-Nitrobenzoyl)-spiro[2-oxazolidinone-5,2'-adamantane] (III)

Compound I (0.33 gram, 1.6 mmol) was treated, first, with sodium methoxide (0.112 gram) in anhydrous methanol, and then with m-nitrobenzoyl chloride (0.37 gram, 2 mmol) (as described in the preceeding example) to give, after workup, 0.495 gram of derivative III, melting point 174° C. (ethanol).

EXAMPLE 4

Preparation of Thiocarbonyl-bis-3,3'spiro[2-oxazolidinone-5,2'-adamantane] (IV)

Compound I (0.90 gram, 5 mmol) was treated with sodium methoxide (0.270 gram, 5 mmol) in anhydrous methanol (stirring at room temperature for 15 minutes). The solvent was evaporated and the residue suspended in toluene. Thiophosgene (0.2 ml) was added and the mixture refluxed for 2 hours. Following workup, 0.17 gram of derivative IV was obtained, melting point 200°–207° C. (ethanol).

EXAMPLE 5

Preparation of Dispiro[adamantane-2,5'-oxazolidine-2',1''-cyclododecane] (VIII)

Cyclododecanone (0.91 gram, 5 mmol) was added to a solution of 2-aminomethyl-2-hydroxyadamantane (0.90 gram, 5 mmol) in 30 ml toluene. After the mixture was refluxed (Dean-Stark separator) for 7 hours, the solvent was evaporated leaving derivative VIII as a brown oil which crystallized from isopropanol, Yield—1.08 gram melting point 241°–245° C. (white crystals from isopropanol).

Dispiro[adamantane-2,5'-oxazolidine-2',8''-tricyclo[5.2.1.0$^{2,6}$]decane] (mp, 110°–112° C.), dispiro[oxazolidine-2,2':5,2''bis-adamantane] (mp 100°–112° C.) and dispiro[adamantane-2,5'-oxazolidine-2',2''-norborane]hydrochloride (mp 234°–235° C.) were prepared in a similar manner by reacting 2-aminomethyl-2-hydroxyadamantane with 8-ketotricyclo[5.2.1.0$^{2,6}$]decane, 2-adamantanone and 2-norbornanone, respectively.

The compounds of the invention are useful as anti-inflammatory, agents.

We claim:

1. A spiro[oxazolidine-5,2'-adamantane] compound having the formula:

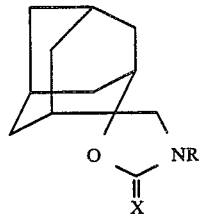

where R is selected from H, benzoyl, nitrobenzoyl and spiro [2-oxazolidinone-5,2'-adamantane]-3-thiocarbonyl; and where X is selected from oxygen, cyclododecane, tricyclo[5.2.1.0$^{2,6}$]decane and norbornane.

2. A compound according to claim 1 where X is oxygen and R is benzoyl or nitrobenzoyl.

3. A compound according to claim 2 wherein the compound is N-(m-nitrobenzoyl)-spiro[2-oxazolidinone-5,2'-adamantane].

4. A compound according to claim 1 wherein the compound is spiro[2-oxazolidinone-5,2'-adamantane].

5. A compound according to claim 1 wherein X is oxygen and R is spiro[2-oxazolidinone-5,2'-adamantane]-3-thiocarbonyl.

6. A compound according to claim 5 wherein the compound is thiocarbonyl bis-3,3'-spiro[2-oxazolidinone-5,2'-adamantane].

7. A compound according to claim 1 wherein X is selected from cyclododecane, tricyclo[5.2.1.0$^{2,6}$]decane and norbornane and R is H.

8. A compound according to claim 7 wherein the compound is dispiro[adamantane-2,5'-oxazolidine-2',8''-tricyclo[5.2.1.0$^{2,6}$]decane].

9. A compound according to claim 7 wherein the compound is dispiro[adamantane-2,5'-oxazolidine-2',2''-norbornane].

10. A compound according to claim 7 wherein the compound is dispiro[adamantane-2,5'-oxazolidine-2',1'''-cyclododecane].

* * * * *